(12) United States Patent
Govari et al.

(10) Patent No.: US 9,173,638 B2
(45) Date of Patent: Nov. 3, 2015

(54) CARDIAC MECHANICAL ASSESSMENT USING ULTRASOUND

(75) Inventors: Assaf Govari, Haifa (IL); Andres Claudio Altmann, Haifa (IL); Alexander Levin, Haifa (IL)

(73) Assignee: Biosense Webster, Inc., Diamond Bar, CA (US)

(*) Notice: Subject to any disclaimer, the term of this patent is extended or adjusted under 35 U.S.C. 154(b) by 1219 days.

(21) Appl. No.: 12/126,032

(22) Filed: May 23, 2008

(65) Prior Publication Data

US 2008/0300487 A1 Dec. 4, 2008

Related U.S. Application Data

(60) Provisional application No. 60/941,778, filed on Jun. 4, 2007.

(51) Int. Cl.
*A61B 8/14* (2006.01)
*A61B 8/00* (2006.01)
(Continued)

(52) U.S. Cl.
CPC ............... *A61B 8/4488* (2013.01); *A61B 5/061* (2013.01); *A61B 8/08* (2013.01); *A61B 8/0883* (2013.01); *A61B 8/12* (2013.01); *A61B 8/4254* (2013.01); *A61B 8/463* (2013.01); *A61B 8/483* (2013.01); *A61B 8/485* (2013.01); *A61B 8/543* (2013.01); *A61B 19/5244* (2013.01); *G01S 7/52038* (2013.01); *G01S 7/52071* (2013.01); *G06T 7/0016* (2013.01); *G06T 7/0083* (2013.01); *G06T 7/2033* (2013.01); *A61B 5/06* (2013.01); *A61B 6/503* (2013.01); *A61B 2019/5251* (2013.01); *A61B 2019/5276* (2013.01); *A61B 2019/5289* (2013.01); *A61B 2019/5295* (2013.01); *G01S 15/8918* (2013.01); *G01S 15/8979* (2013.01); *G06T 2207/10076* (2013.01); *G06T 2207/30048* (2013.01)

(58) Field of Classification Search
CPC ............... A61B 18/1492; A61B 18/24; A61B 2019/5276
USPC .................................................. 600/437–461
See application file for complete search history.

(56) References Cited

U.S. PATENT DOCUMENTS 5,515,849 A * 5/1996 Murashita et al. ............ 600/479
5,622,174 A   4/1997 Yamazaki
(Continued)

FOREIGN PATENT DOCUMENTS

EP    H09-327458    12/1997
EP    0961135       12/1999
(Continued)

OTHER PUBLICATIONS

Stoylen, A. Strain Rate Imaging of the Left Ventricle by Ultrasound. Norwegian University of Science and Technology, Faculty of Medicine, 2001.
(Continued)

*Primary Examiner* — Elmer Chao
(74) *Attorney, Agent, or Firm* — Louis J. Capezzuto

(57) ABSTRACT

A method for diagnosis includes capturing a sequence of two-dimensional ultrasound images of a moving organ within a body of a patient. At least one contour of the organ is identified in a succession of the images in the sequence and is processed to generate an output indicative of motion of the organ over time.

28 Claims, 3 Drawing Sheets

(51) Int. Cl.
*A61B 8/08* (2006.01)
*A61B 8/12* (2006.01)
*A61B 19/00* (2006.01)
*G01S 7/52* (2006.01)
*G06T 7/00* (2006.01)
*G06T 7/20* (2006.01)
*A61B 5/06* (2006.01)
*A61B 6/00* (2006.01)
*G01S 15/89* (2006.01)

(56) References Cited

U.S. PATENT DOCUMENTS

| | | | |
|---|---|---|---|
| 5,694,945 A * | 12/1997 | Ben-Haim | 600/407 |
| 5,738,096 A | 4/1998 | Ben-Haim | |
| 5,797,849 A * | 8/1998 | Vesely et al. | 600/461 |
| 5,876,345 A * | 3/1999 | Eaton et al. | 600/466 |
| 6,004,269 A | 12/1999 | Crowley et al. | |
| 6,139,500 A | 10/2000 | Clark | |
| 6,332,089 B1 | 12/2001 | Acker et al. | |
| 6,447,453 B1 | 9/2002 | Roundhill et al. | |
| 6,447,454 B1 | 9/2002 | Chenal et al. | |
| 6,556,695 B1 | 4/2003 | Packer et al. | |
| 6,618,612 B1 | 9/2003 | Acker et al. | |
| 6,690,963 B2 | 2/2004 | Ben-Haim et al. | |
| 6,716,166 B2 | 4/2004 | Govari | |
| 6,773,402 B2 | 8/2004 | Govari et al. | |
| 2001/0024516 A1 | 9/2001 | Yoshioka et al. | |
| 2002/0065455 A1 | 5/2002 | Ben-Haim et al. | |
| 2002/0173693 A1 * | 11/2002 | Landesberg | 600/16 |
| 2004/0015081 A1 | 1/2004 | Kramer et al. | |
| 2004/0068178 A1 | 4/2004 | Govari | |
| 2004/0147920 A1 | 7/2004 | Keidar | |
| 2005/0014377 A1 | 1/2005 | Kamada | |
| 2005/0020917 A1 * | 1/2005 | Scherch | 600/437 |
| 2005/0027320 A1 * | 2/2005 | Nehls et al. | 607/9 |
| 2005/0137661 A1 * | 6/2005 | Sra | 607/96 |
| 2005/0143777 A1 | 6/2005 | Sra | |
| 2005/0187461 A1 * | 8/2005 | Murphy et al. | 600/416 |
| 2005/0283075 A1 | 12/2005 | Ma et al. | |
| 2006/0241445 A1 * | 10/2006 | Altmann et al. | 600/443 |
| 2007/0106146 A1 | 5/2007 | Altmann et al. | |
| 2007/0118041 A1 | 5/2007 | Nishiura et al. | |
| 2007/0167801 A1 * | 7/2007 | Webler et al. | 600/459 |

FOREIGN PATENT DOCUMENTS

| | | |
|---|---|---|
| EP | 0813074 B1 | 9/2001 |
| EP | 1720039 | 11/2006 |
| JP | H06-114059 | 4/1994 |
| JP | 2007-117611 | 5/2007 |
| JP | 2007-117746 | 5/2007 |
| WO | WO 98/46139 | 10/1998 |
| WO | WO 99/55233 | 11/1999 |
| WO | WO 00/19908 | 4/2000 |
| WO | WO 01/20552 | 3/2001 |
| WO | WO 2007/021511 | 2/2007 |

OTHER PUBLICATIONS

Extended European Search Report re: 08251923.2 dated Jan. 5, 2009.
Australian Patent Examination Report dated Jan. 14, 2013 received from related Australian Application No. 2008202449.
Japanese Reporting Letter dated Sep. 4, 2013 for corresponding Patent Application No. JP2008-145705.
Japanese Reporting Letter dated Dec. 10, 2013 for corresponding Patent Application No. JP2008-145705.
Canadian Reporting Letter dated Dec. 9, 2014 for corresponding Patent Application No. CA 2,633,231.
Australian Reporting Letter dated Jan. 14, 2013 for corresponding Patent Application No. CA 2008202449.

* cited by examiner

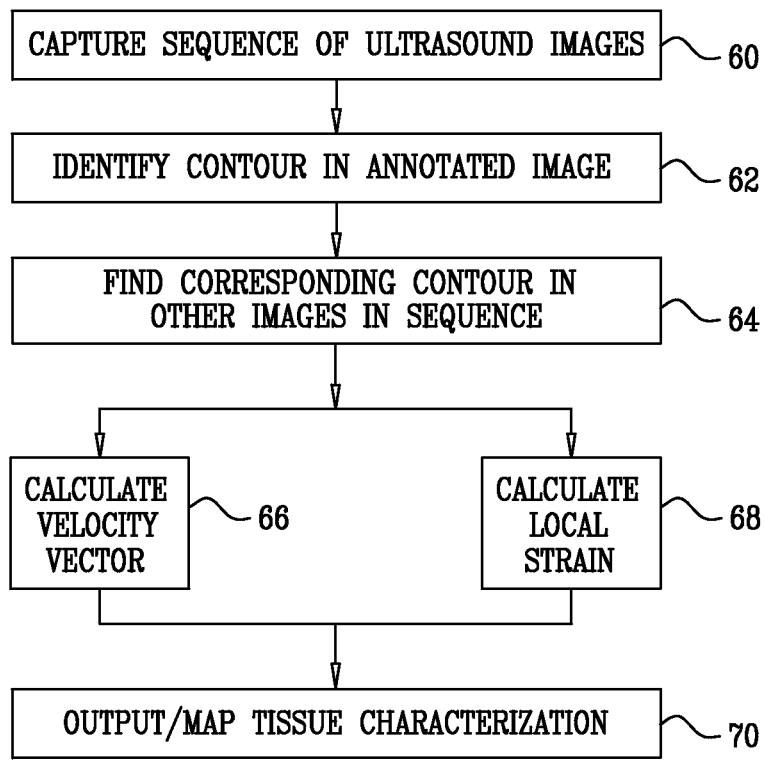
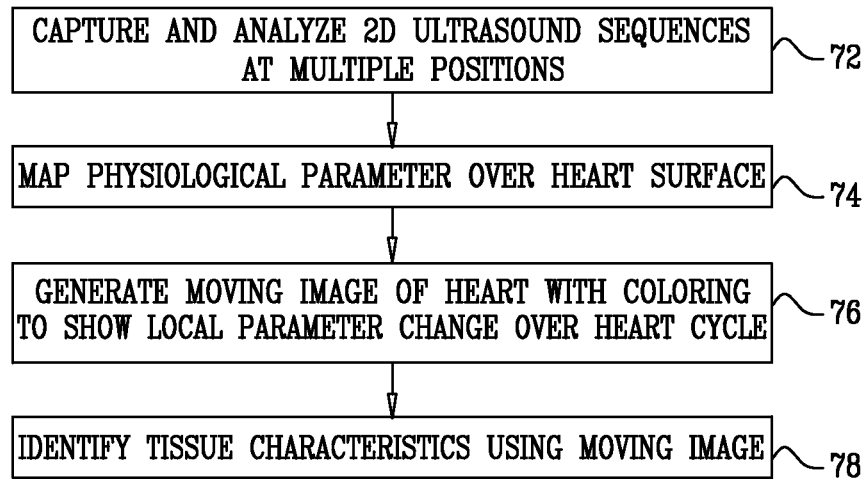

CARDIAC MECHANICAL ASSESSMENT USING ULTRASOUND

CROSS-REFERENCE TO RELATED APPLICATION

This application claims the benefit of U.S. Provisional patent application 60/941,778, filed Jun. 4, 2007, which is incorporated herein by reference.

FIELD OF THE INVENTION

The present invention relates generally to systems and methods for medical diagnosis, and specifically to systems and methods for assessing the function of a moving organ, such as the heart.

BACKGROUND OF THE INVENTION

Methods for three-dimensional (3-D) mapping of the endocardium (i.e., the inner surfaces of the heart) are known in the art. For example, U.S. Pat. No. 5,738,096, whose disclosure is incorporated herein by reference, describes a method for constructing a map of the heart. An invasive probe is brought into contact with multiple locations on the wall of the heart. The position of the invasive probe is determined for each location, and the positions are combined to form a structural map of at least a portion of the heart.

In some systems, such as the one described by U.S. Pat. No. 5,738,096 cited above, additional physiological properties, as well as local electrical activity on the surface of the heart, are also acquired by the catheter. A corresponding map incorporates the acquired local information.

Some systems use hybrid catheters that incorporate ultrasound imaging and position sensing, as well as electrical sensing. For example, U.S. Pat. No. 6,690,963, whose disclosure is incorporated herein by reference, describes a locating system for determining the location and orientation of an invasive medical instrument that may include an ultrasound imaging head, as well as an electrode.

A catheter with acoustic transducers may be used for non-contact imaging of the endocardium. For example, U.S. Pat. Nos. 6,716,166 and 6,773,402, whose disclosures are also incorporated herein by reference, describe a system for 3-D mapping and geometrical reconstruction of body cavities, particularly of the heart.

As another example, U.S. Pat. No. 5,876,345, whose disclosure is incorporated herein by reference, describes an ultrasonic catheter for two-dimensional (2-D) imaging or 3-D reconstruction. The ultrasonic catheter includes at least two ultrasonic arrays having good near and far field resolutions. The catheter provides an outline of a heart chamber, in order to assist in interpreting images obtained by the catheter.

Several methods are known in the art for non-contact reconstruction of the endocardial surface using intracardial ultrasonic imaging. For example, PCT Patent Publication WO 00/19908, whose disclosure is incorporated herein by reference, describes a steerable transducer array for intracardial ultrasonic imaging. The array forms an ultrasonic beam, which is steered in a desired direction by an active aperture. U.S. Pat. No. 6,004,269, whose disclosure is also incorporated herein by reference, describes an acoustic imaging system based on an ultrasound device that is incorporated into a catheter. The ultrasound device directs ultrasonic signals toward an internal structure in the heart to create an ultrasonic image.

PCT Patent Publication WO 99/55233, whose disclosure is incorporated herein by reference, describes a method for delineating a 3-D surface of a patient's heart. A 3-D mesh model is developed using training data, to serve as an archetypal shape for a population of patient hearts. Multiple ultrasound images of the patient's heart are taken in different image planes. Anatomical locations are manually identified in each of the images. The mesh model is rigidly aligned with the images, in respect to the predefined anatomical locations.

Other methods of contour extraction and 3-D modeling using ultrasonic images are described in European Patent Application EP 0961135, whose disclosure is incorporated herein by reference. As another example, PCT Patent Publication WO 98/46139, whose disclosure is also incorporated herein by reference, describes a method for combining Doppler and B-mode ultrasonic image signals into a single image using a modulated nonlinear mapping function.

U.S. Patent Application Publication 2006/0241445, whose disclosure is incorporated herein by reference, describes a method for modeling of an anatomical structure. A plurality of ultrasonic images of the anatomical structure are acquired using an ultrasonic sensor, at a respective plurality of spatial positions of the ultrasonic sensor. Location and orientation coordinates of the ultrasonic sensor are measured at each of the plurality of spatial positions. Contours-of-interest that refer to features of the anatomical structure are marked in one or more of the ultrasonic images. A three-dimensional (3-D) model of the anatomical structure is constructed, based on the contours-of-interest and on the measured location and orientation coordinates.

Other patents and patent applications of relevance to the present invention include U.S. Pat. No. 6,139,500, U.S. Patent Application Publication 2005/0283075, U.S. Pat. Nos. 6,447,453 and 6,447,454, U.S. Patent Application Publication 2005/014377, U.S. Patent Application Publication 2005/0137661, and U.S. Pat. No. 6,556,695, all of which are incorporated herein by reference.

SUMMARY OF THE INVENTION

Embodiments of the present invention that are described hereinbelow provide improved methods for modeling and analyzing motion of organs in the body, and particularly of the heart.

In some of these embodiments, an acoustic imaging probe, such as an ultrasound catheter within the heart, captures a sequence of 2-D images as the heart beats. Contours of a heart chamber are identified, either automatically or manually, in one of the 2-D images. An image processor then automatically identifies these contours in the other images in the sequence. The image processor may analyze changes in the contours during the heart cycle in order to determine parameters of motion of the heart wall, such as local velocity and strain.

Additionally or alternatively, the image processor may use the contours in segmenting the images and reconstructing a "4-D" image of the heart, i.e., a 3-D anatomical image that changes over time, showing the motion of the heart. The moving image may be enhanced, by addition of pseudocolor, for example, to show changes over time in other physiological parameters, such as local electrical parameters measured by a catheter inside the heart.

There is therefore provided, in accordance with an embodiment of the present invention, a method for diagnosis, including:

capturing a sequence of two-dimensional ultrasound images of a moving organ within a body of a patient;

identifying at least one contour of the organ in a succession of the images in the sequence; and processing the at least one identified contour to generate an output indicative of motion of the organ over time.

Processing the at least one identified contour may include computing a displacement of the contour over a period of cyclical movement of the organ, a velocity vector of one or more segments of the contour, or a strain in the organ responsively to a change in length of the contour.

In disclosed embodiments, the moving organ is a heart of the patient, and processing the at least one identified contour includes analyzing the motion of a wall of at least one chamber of the heart over one or more cycles of the heart. Typically, capturing the sequence of the two-dimensional ultrasound images includes inserting a catheter, including an acoustic transducer and a position sensor, into the heart, and capturing the two-dimensional ultrasound images using the transducer while tracking coordinates of the catheter using the position sensor. In one embodiment, analyzing the motion of the wall includes find a location of scar tissue in the wall responsively to the motion. In another embodiment, analyzing the motion of the wall includes comparing the motion of two or more chambers of the heart so as to detect improper synchronization of the motion of the chambers.

There is also provided, in accordance with an embodiment of the present invention, a method for diagnosis, including:

capturing multiple ultrasound input images of a moving organ within a body of a patient;

collecting data that are indicative of respective local values of a physiological parameter at locations on a surface of the moving organ; and generating a sequence of three-dimensional images, responsively to the input images and the collected data, showing movement of the organ while superimposing an indication of changes in the local values on the surface in the three-dimensional images as the organ moves in the three-dimensional images in the sequence.

In some embodiments, capturing the multiple ultrasound input images includes capturing two-dimensional ultrasound images from multiple different positions of an acoustic transducer, and recording location and orientation coordinates of the acoustic transducer in the multiple different positions, and generating the sequence includes combining the two-dimensional ultrasound images using the location and orientation coordinates to reconstruct the three-dimensional images. Typically, capturing the two-dimensional ultrasound images includes recording respective times of capture of the two-dimensional ultrasound images relative to an annotation point in a cycle of motion of the organ, and combining the two-dimensional ultrasound images includes grouping the two-dimensional ultrasound images according to the respective times of capture in order to generate the three-dimensional images corresponding to the respective times in the cycle. In a disclosed embodiment, the moving organ is a heart of the patient, and capturing the two-dimensional ultrasound images includes inserting a catheter, including the acoustic transducer and a position sensor, into the heart, and capturing the two-dimensional ultrasound images using the transducer while tracking coordinates of the catheter using the position sensor.

Typically, generating the sequence includes coloring the surface of the moving organ in the three-dimensional images responsively to the values of physiological parameter. In a disclosed embodiment, the moving organ is a heart of the patient, and collecting the data includes collecting electrical data, and coloring the surface includes displaying variations in electrical activity of the heart over an area of a chamber of the heart in the course of one or more heart cycles.

There is additionally provided, in accordance with an embodiment of the present invention, diagnostic apparatus, including:

an acoustic transducer, which is configured to capture a sequence of two-dimensional ultrasound images of a moving organ within a body of a patient; and an image processor, which is configured to identify at least one contour of the organ in a succession of the images in the sequence, and to process the at least one identified contour to generate an output indicative of motion of the organ over time.

There is further provided, in accordance with an embodiment of the present invention, diagnostic apparatus, including:

an acoustic transducer, which is configured to capture multiple ultrasound input images of a moving organ within a body of a patient;

an invasive probe, which is configured to collect data that are indicative of respective local values of a physiological parameter at locations on a surface of the moving organ; and an image processor which is configured to generate, responsively to the input images and the collected data, a sequence of three-dimensional images showing movement of the organ while superimposing an indication of changes in the local values on the surface in the three-dimensional images as the organ moves in the three-dimensional images in the sequence.

The present invention will be more fully understood from the following detailed description of the embodiments thereof, taken together with the drawings in which:

BRIEF DESCRIPTION OF THE DRAWINGS

FIG. 5 is a flow chart that schematically illustrates a method for heart tissue characterization, in accordance with an embodiment of the present invention; and FIG. 6 is a flow chart that schematically illustrates a method for cardiac imaging, in accordance with an embodiment of the present invention.

DETAILED DESCRIPTION OF EMBODIMENTS

System Description

Figure 1:
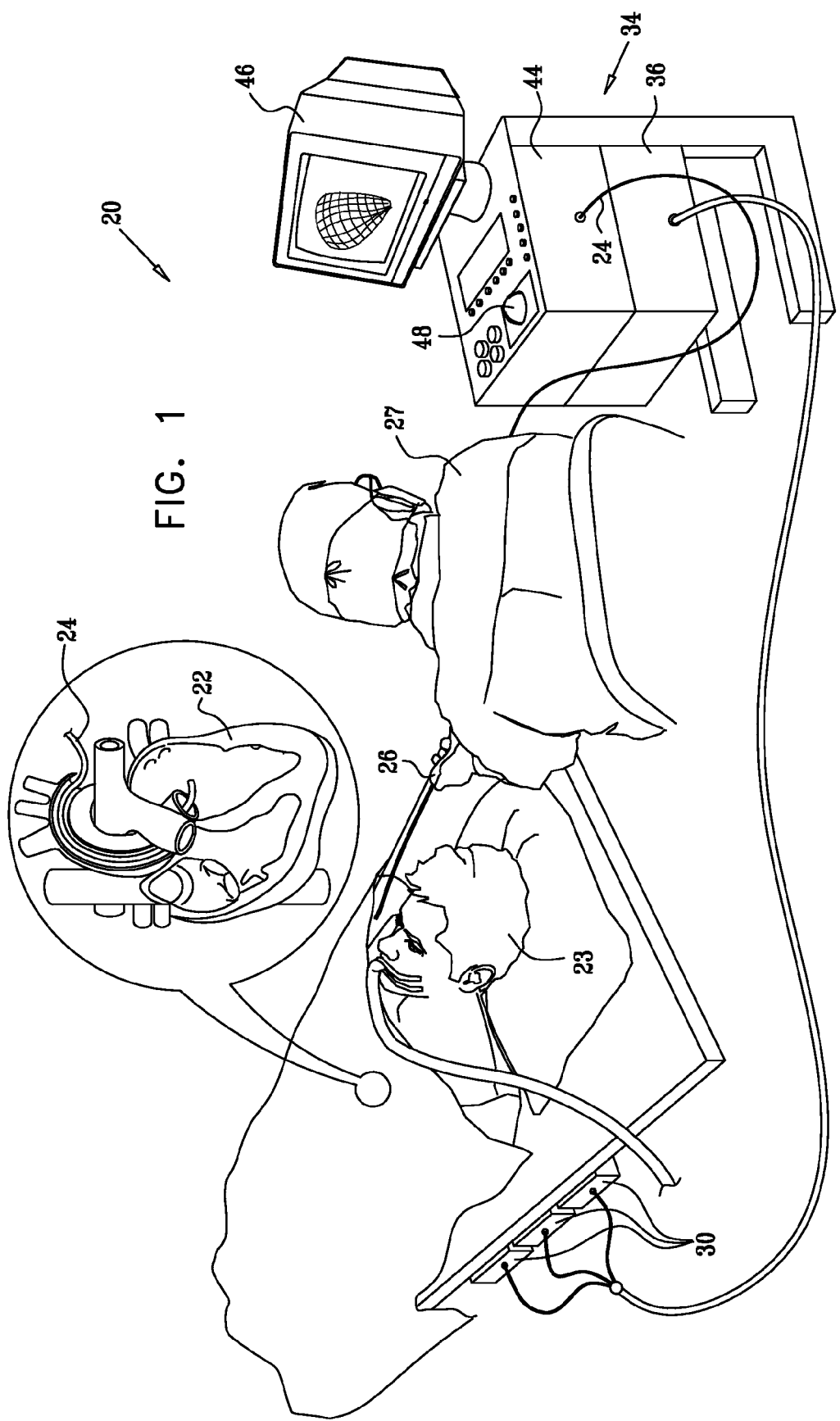
FIG. 1 is a schematic, pictorial illustration of a system for cardiac mapping and imaging, in accordance with an embodiment of the present invention.
Figure 2:
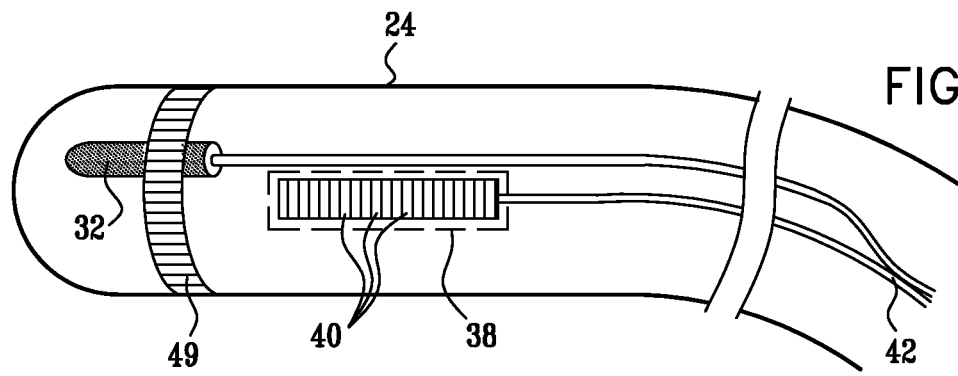
FIG. 2 is a schematic side view of the distal end of a catheter, in accordance with an embodiment of the present invention.

Reference is now made to FIGS. 1 and 2, which schematically illustrate a system 20 for imaging and mapping a heart 22 of a patient 23, in accordance with an embodiment of the present invention. The system comprises a catheter 24, which is inserted by a physician 27 into a chamber of the heart through a vein or artery. FIG. 1 is a pictorial view of the system as a whole, while FIG. 2 shows details of the distal end of the catheter.

Catheter 24 is used, as described hereinbelow, to acquire ultrasound images inside the heart and may, in some embodiments, acquire other local physiological data, as well, such as electophysiological data. Catheter 24 typically comprises a handle 26 for operation of the catheter by the physician. Suitable controls (not shown) on the handle enable the physician to steer, position and orient the distal end of the catheter as desired. Alternatively, the principles of the present invention may be implemented using images captured by ultrasound probes of other types, such as a transesophageal probe or a non-invasive trans-thoracic probe.

System 20 comprises a positioning sub-system that measures location and orientation coordinates of catheter 24. (Throughout this patent application and in the claims, the term "location" refers to the spatial coordinates of the catheter, and the term "orientation" refers to its angular coordinates. The term "position" refers to the full positional information of the catheter, comprising both location and orientation coordinates.)

In one embodiment, the positioning sub-system comprises a magnetic position tracking system that determines the location and orientation of catheter 24. The positioning sub-system generates magnetic fields in a predefined working volume its vicinity and senses these fields at the catheter. For this purpose, the positioning sub-system typically comprises a set of external radiators, such as field generating coils 30, which are located in fixed, known positions external to the patient and generate electromagnetic fields in the vicinity of heart 22. The generated fields are sensed by a position sensor 32 inside catheter 24. In an alternative embodiment, a radiator, such as a coil, in the catheter generates electromagnetic fields, which are received by sensors outside the patient's body.

Position sensor 32 transmits, in response to the sensed fields, position-related electrical signals over cables 40 running through the catheter to a console 34. Alternatively, the position sensor may transmit signals to the console over a wireless link. The console comprises a positioning processor 36, which controls coils 30 and calculates the location and orientation of the distal end of catheter 24 based on the signals sent by position sensor 32. Positioning processor 36 typically receives, amplifies, filters, digitizes, and otherwise processes signals from catheter 24.

Some position tracking systems that may be used for this purpose are described, for example, in U.S. Pat. Nos. 6,690,963, 6,618,612 and 6,332,089, and U.S. Patent Application Publications 2002/0065455 A1, 2004/0147920 A1 and 2004/0068178 A1, whose disclosures are all incorporated herein by reference. Although the positioning sub-system shown in FIG. 1 uses magnetic fields, the methods described below may likewise be implemented using any other suitable positioning sub-system, such as systems based on electrical impedance, acoustic or ultrasonic measurements.

System 20 enables physician 27 to perform a variety of mapping and imaging procedures, including display and analysis of two-dimensional (2-D) ultrasound images, as well as reconstruction of three-dimensional (3-D) images of target structures, such as chambers of the heart, based on the 2-D ultrasound images. The system can also register, overlay and display a parametric map, such as an electrophysiological information map or an electro-anatomical on the ultrasound images, as well as registering the ultrasound images with a 3-D image acquired from an external system, such as a computed tomography (CT) or magnetic resonance imaging (MRI) system. Some of these aspects of system 20 are described in the above-mentioned US 2006/0241445, while other novel aspects are described further hereinbelow.

As shown in FIG. 2, the distal end of catheter 24 comprises an ultrasound imaging sensor 38, which typically comprises an array of ultrasonic transducers 40, such as piezo-electric transducers. Transducers 40 operate as a phased array, jointly transmitting an acoustic beam. (Although the transducers are shown arranged in a linear array configuration, other array configurations can be used, such as circular or convex configurations.) In one embodiment, the array transmits a short burst of ultrasound energy and then switches to a receiving mode for receiving the ultrasound signals reflected from the surrounding tissue.

Typically, transducers 40 are driven individually in a controlled manner in order to steer the ultrasound beam in a desired direction. By appropriate timing of the transducers, the ultrasound beam can produced by sensor 38 be given a concentrically curved wave front, so as to focus the beam at a given distance from the transducer array. Thus, system 20 uses the transducer array as a phased array and implements a transmit/receive scanning mechanism that enables the steering and focusing of the ultrasound beam, so as to produce 2-D ultrasound images.

After receiving the reflected ultrasound echoes, transducers 30 send electric signals based on the reflected echoes over cables 42 through catheter 24 to an image processor 44 in console 34. The image processor transforms the signals into 2-D ultrasound images, which are typically sector-shaped. Image processor 44 typically computes or receives catheter position information from positioning processor 36 and uses this information in performing image reconstruction and analysis functions, which are described in greater detail below. In some embodiments, the image processor uses the ultrasound images and the positional information to produce a 3-D image or 4-D image sequence of a target structure, which is presented to the physician as a 2-D projection on a display 46. The physician may interact with the displayed image and with console 34 generally by means of a user interface device 48, such as a trackball or other pointing device.

In some embodiments, the distal end of catheter 24 also comprises at least one electrode 49 for performing diagnostic and/or therapeutic functions, such as electrophysiological mapping and/or radio frequency (RF) ablation. In one embodiment, electrode 49 is used for sensing local electrical potentials. The electrical potentials measured by electrode 49 may be used in mapping the local electrical activity on the endocardial surface. When electrode 49 is brought into contact or proximity with a point on the inner surface of the heart, it measures the local electrical potential at that point. The measured potentials are converted into electrical signals and sent through the catheter to the image processor for processing and display. In other embodiments, the local electrical potentials are obtained from another probe, such as a second catheter (not shown in the figures), comprising suitable electrodes and a position sensor, all connected to console 34.

In alternative embodiments, catheter 24 may comprise sensors in other configurations. For example, although electrode 49 is shown as being a single ring electrode, the catheter may comprise any number of electrodes in any form. Additionally or alternatively, the catheter may sense other physiological parameters, such as various tissue characteristics, temperature and/or blood flow.

Position sensor 32 is typically located within the distal end of catheter 24, adjacent to electrode 49 and transducers 40. Typically, the mutual locational and orientational offsets between the position sensor, electrode, and transducers are constant. These offsets are used by positioning processor 36 to derive the coordinates of ultrasonic sensor 38 and of electrode 49, given the measured position of position sensor 32. Further characteristics of the position sensor and its use are described in the above-mentioned US 2006/0241445.

Typically, both the ultrasound images and the position measurements are synchronized with the heart cycle, by gating signal and image capture relative to a body-surface electrocardiogram (ECG) signal or intra-cardiac electrocardiogram. Since features of the heart change their shape and position during the heart's periodic contraction and relaxation, console 34 records the timing of each image captured by sensor 38 relative to an annotation point (such as the QRS peak of the ECG) in the heart cycle, along with the corresponding position measurement. Thus, the images may be grouped according to the different points in the heart cycle at which they were captured. In some embodiments, additional measurements taken by the catheter, such as measurements of electrical and other tissue characteristics, are also synchronized to the ECG signal, as well as with the corresponding position measurements. The results of these additional measurements may then be overlaid on the reconstructed 3-D ultrasound image, as described further hereinbelow.

Typically, positioning processor 36 and image processor 44 comprise one or more general-purpose computer processors, which are programmed in software to carry out the functions described herein. The software may be downloaded to the computer in electrical form, over a network, for example, or it may, alternatively or additionally, be stored on tangible media, such as optical, magnetic or electronic memory media. The positioning processor and image processor may be implemented using separate computers or using a single computer, or may be integrated with other computing functions of system 20. Additionally or alternatively, at least some of the positioning and image processing functions may be performed using dedicated hardware.

Tracking and Analysis of Contours

Figure 3:
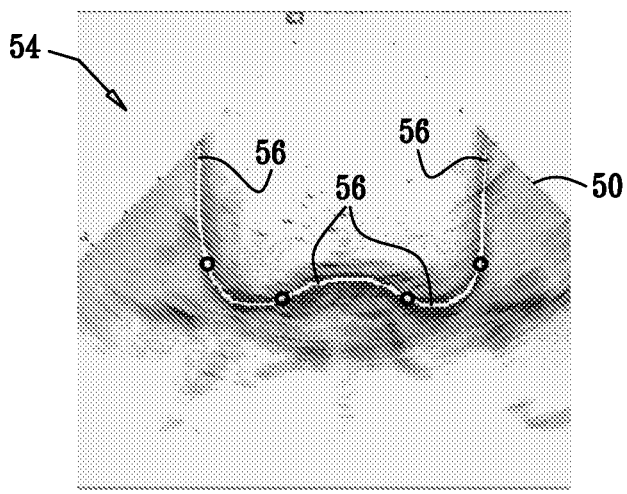
FIGS. 3 and 4 are schematic representation of ultrasound images of a heart chamber at different, respective points in the heart cycle, showing a moving contour of the heart chamber in accordance with an embodiment of the present invention.
Figure 4:
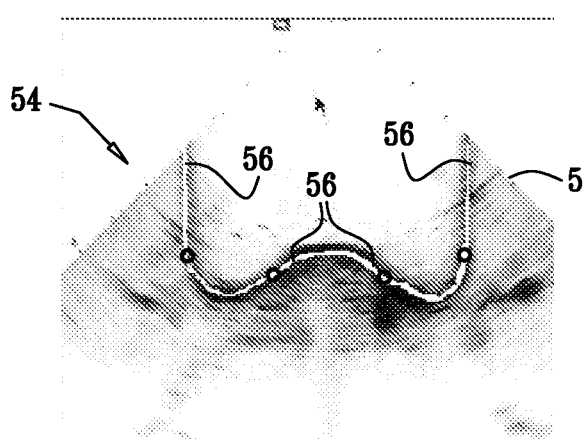

Reference is now made to FIGS. 3-5, which schematically illustrate a method for heart tissue characterization based on ultrasound images, in accordance with an embodiment of the present invention. FIGS. 3 and 4 show 2-D ultrasound images 50 and 52, respectively, of heart 22, which are used in the method, while FIG. 5 is a flow chart that presents the steps of the method itself. Images 50 and 52 are processed by image processor 44 to identify contours 54 and to perform other functions that are described hereinbelow on the basis of these contours. As noted earlier, images for this sort of processing may be acquired not only using an ultrasound catheter, but also using any other suitable type of acoustic imaging system that is known in the art.

To acquire images 50 and 52, the user (such as physician 27) moves catheter 24 inside the heart until the desired point of view is achieved, such as the view shown in FIGS. 3 and 4. The user then operates system 20 to capture a "clip," i.e., a sequence of 2-D ultrasound images at the desired position, at an image capture step 60. The images show a certain "slice" of a heart chamber and the surrounding tissue at multiple points in time over the course of one or more heart cycles. (Typically the clip is about 2.5 seconds long.)

The user freezes an ultrasound image in the sequence and draws contour 54 on the 2-D image, at a contour identification step 62. Alternatively or additionally, processor 44 may apply automatic edge detection to locate the contour. The image is marked with the point in the heart cycle at which it was captured. Typically, as noted earlier, the timing of the image is marked relative to an annotation point in the electrocardiogram (ECG) signal, which is captured using skin-surface electrodes and a suitable monitor (not shown), but any other suitable means for identifying the annotation point may alternatively be used. FIGS. 3 and 4 show a contour of one chamber of the heart, but the methods described herein may similarly be applied to multiple contours of multiple chambers.

Contour 54 is initially drawn on one of the images in the sequence, typically (although not necessarily) the image captured at the annotation point itself. For the sake of illustration, it will be assumed that image 50 is the annotation image on which the contour is initially drawn. After contour 54 has been drawn on image 50, image processor 44 uses this contour to find the corresponding image contours in all the other images of the image sequence between successive annotation points, at a contour propagation step 64. Thus, based on contour 54 in image 50, the image processor finds the corresponding contour in image 52. The frame rate in the video sequence is typically 30 frames per second, but rates up to 100 frames per second may enable better estimation of the tissue characteristics.

In addition to detecting the contours, image processor 44 may calculate velocity vectors, corresponding to the movement of a contour or contours during the sequence, at a velocity calculation step 66. To determine the local velocity of segments 56 of a contour, for example, the image processor sweeps a rectangular window over the selected contour in successive image frames. Any suitable window size may be used, for example, 5×10 pixels. The processor computes a correlation function between windows from the successive frames as a function of displacement between the windows. The movement in the x and y directions that maximizes the correlation function gives the local displacement of the contour in the window in x and y directions. Knowing the time difference between successive frames and the displacement, the local velocity can be calculated as the quotient of the displacement divided by the time difference. The velocity vector is the combination of the velocity components in the x and y directions.

Referring to FIGS. 3 and 4, it can be seen that the segments in the central part of contour 54 have velocity components mainly in the upward direction.

The image processor may also perform strain analysis, at a local strain calculation step 68. To compute the strain along contour 54, the contour is segmented into a number of segments 56 of known length. In the subsequent image frame, the same contour is identified and segmented into the same number of segments. The difference between the lengths of two corresponding segments from the two frames divided by the length of the segment in the first frame gives the strain on the segment.

Further information regarding strain computations of this sort are presented by Stoylen in a thesis entitled, "Strain Rate Imaging of the Left Ventricle by Ultrasound," Norwegian University of Science and Technology (2001), which is available at http://folk.ntnu.no/stoylen/strainrate/thesis_AS.pdf and is incorporated herein by reference.

Other calculations can also be done on the identified moving contours. For example, the displacement of contours and segments of contours during the heart cycle may be calculated.

Image processor 44 outputs the calculation results, at an output step 70, typically by showing 2-D or 3-D images on display 46. The results can be displayed on the actual ultrasound images in the video sequence, for example, showing the identified contours and the calculated parameters (velocity vectors, strain, etc.) The magnitudes of a parameter of interest over segments 56 may be shown by color-coding the segments accordingly.

The parameters that are derived and output in this manner may be used in characterizing the tissue, either automatically by processor 44 or visually by a user of system 20. Anomalies in the velocity and/or displacement of certain contour segments can be used, for example, for scar tissue identification (particularly in combination with information provided by other imaging modalities, such as MRI). As another example, differences in the instantaneous velocity between contours in different parts of the heart (such as in different chambers) can be used to assess the synchronization between the chamber walls, as well as other diagnostic indicators of the mechanical functioning of the heart. Some of these indicators may be combined with electrophysiological diagnostic information, which may be provided by catheter 24 or by another mapping catheter within the heart. For example, some of the methods for cardiac mechanical and electromechanical diagnosis that are described in the above-mentioned U.S. Pat. No. 5,738,096 may also be applied, mutatis mutandis, using the diagnostic information provided by the moving contours that are detected in ultrasound images as described above.

4-D Image Sequences Based on Contour Mapping

FIG. 6 is a flow chart that schematically illustrates a method for cardiac imaging, in accordance with an embodiment of the present invention. In this method, the moving contours provided by sequences of ultrasound images are combined with electro-anatomical mapping data, such as the type data produced by the CARTO mapping system (Biosense Inc., Diamond Bar, Calif.).

A user, such as physician 27, aims catheter 24 in a desired direction in heart 22, and captures a clip of 2-D ultrasound images, at an image capture step 72. The user operates the system as described above with reference to FIG. 5 so as to identify contours in all the frames in the clip. The user then moves the catheter, captures another clip of images, and identifies new contours if necessary. Alternatively, the user may move the catheter continually while acquiring the images. In any case, as explained above, each of the ultrasound images is associated with a certain point in time relative to an annotation point in the heart cycle and the position of the catheter at which the image was recorded. Each image is thus marked with the time of acquisition, relative to the annotation point, and with the catheter position coordinates at the time of acquisition.

In addition, for each time slot in the heart cycle, a corresponding CARTO map is generated, at a mapping step 74. For example, at a frame rate of 30 frames per second, there will be maps in time slots of 33 ms. For this purpose, the user brings electrode 46 on catheter 24 (or an electrode or electrodes on a separate mapping catheter) into contact with points on the inner surface of one or more of the heart chambers. Although steps 72 and 74 are shown in FIG. 6 as occurring separately and sequentially, the order of these steps may be reversed, or the steps may be interleaved, without any particular constraints on the order of acquisition of ultrasound images relative to acquisition of electrical mapping data.

When the user has finished imaging, mapping and identifying all the desired contours, image processor 44 produces a moving image of the heart overlaid with an electro-anatomical CARTO map for every time slot, at an image output step 76. The image processor uses the position data provided by position sensor 32 in the catheter in order to align the ultrasound images with the CARTO data in the same 3-D coordinate frame. Each contour in the ultrasound images is thus associated with the CARTO map for the corresponding time slot. The geometrical shape of the CARTO map may be updated according to the contours, as described, for example, in the above-mentioned US 2006/0241445, as well as in U.S. Patent Application Publication 2007/0106146, whose disclosure is also incorporated herein by reference.

To reconstruct 3-D and 4-D images, the 2-D fan images are grouped by acquisition time (relative to the heart cycle). Typically, the images are divided into between fifteen and thirty time groups in this manner. The images in each group are then combined, using the location and orientation coordinates, into a 3-D volume matrix. In other words, the images are stored in 3-D matrices, with a corresponding matrix for each time slot. System 20 may give the user an indication of the amount of data acquired in each time slot matrix so as to assist the user in knowing when to terminate data acquisition. To segment the 3-D images, processor 44 may select a seed point inside the heart chamber that is to be segmented. It then spreads the chamber volume outward from this seed point in order to segment the chamber, using the contours that were found at step 72. Alternatively, other methods that are known in the art may be used to reconstruct the surfaces of the heart chamber. At the conclusion of this stage, for each time slot there is a segmented CT-like image generated from the 3-D volume.

Following step 76, processor 44 is able to display the moving volumes of the heart using 3-D volume-rendering techniques, with numbers or other visual cues to show the electrical activity on the inner heart surface. These 3-D images can be displayed as a clip, showing the heart motion and electrical activity in a "four-dimensional" (4-D-3-D plus time) display. By interpolation of the electrical activity in the CARTO maps, the electrical parameters of interest may be interpolated over the entire heart wall surface, and the map of the heart can be colored according to the parameters. The colors change and move over the course of each heart cycle, thereby enabling the user to visualize the interaction between the electrical and mechanical activity of the heart. Other parameters, such as temperature or chemical parameters, may be displayed in 4-D in a similar manner. Alternatively, upon the user's command, system 20 may display only the moving contours, and optionally the calculated mechanical parameters, such as the velocity vector and strain, that were described above. Volume calculations can also be performed on the 4-D images.

The user of system 20 views and analyzes the moving images in order to identify characteristics of the heart tissue, at a diagnosis step 78. For example, the user may identify areas of scar tissue based on their weak electrical parameters and deviant mechanical behavior. As another example, the user may use the moving images to diagnose improper coordination between different chambers of the heart, as expressed by abnormal timing of mechanical and/or electrical changes over the course of a heart cycle. Such abnormalities typically occur, for example, in congestive heart failure. The user may then apply the visual information provided by system 20 in deciding where to place pacing leads in the heart for purposes of cardiac resynchronization therapy or to meet other therapeutic goals.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A method for diagnosis of a beating heart, comprising:
providing a catheter having a position sensor configured to transmit signals used to determine location and orientation coordinates of a distal end of the catheter in a 3-D coordinate frame of reference and an ultrasonic imaging sensor configured to transmit and receive signals used to determine two-dimensional (2D) ultrasound images;
inserting the catheter into a chamber of the beating heart;

capturing on an image processor a sequence of two-dimensional (2D) ultrasound images of the beating heart using the catheter the chamber of the heart of a patient, each of the two-dimensional (2D) ultrasound images being associated with a point in time relative to an annotation point in the heart cycle and a location and orientation coordinate of the distal end of the catheter at the point in time relative to the annotation point in time;

creating an electroanatomical map of the chamber of the beating heart within the 3-D coordinate frame of reference;

displaying a video of the sequence of 2D images in succession to show motion of the beating heart;

overlaying the electroanatomical map on the video of the motion of the beating heart using the location and orientation coordinates of the distal end of the catheter at each point in time relative to the annotation point in time;

freezing the video to display one of the 2D images of the sequence;

identifying at least one contour of the beating heart on the one frozen image;

finding the identified at least one contour in each of the other images in the sequence of 2D images;

analyzing changes in the identified at least one contour in the sequence of 2D images based on the motion of the beating heart by computing a displacement of the identified at least one contour over a period of cyclical movement of the beating heart;

generating an output in response to analyzing changes of the identified at least one contour; and displaying the output on the video of the sequence of 2D images.

2. The method according to claim 1, wherein analyzing changes in the identified at least one contour comprises computing a velocity vector of one or more segments of the contour.

3. The method according to claim 1, wherein analyzing changes in the identified at least one contour comprises computing a strain in the beating heart responsively to a change in length of the contour.

4. The method according to claim 1, wherein analyzing changes in the identified at least one contour comprises analyzing the motion of a wall of at least one chamber of the heart over one or more cycles of the heart.

5. The method according to claim 4, wherein the ultrasonic imaging sensor of the catheter further comprise an acoustic transducer and further comprises capturing the two-dimensional ultrasound images using the transducer while tracking location and orientation coordinates of the catheter using the position sensor.

6. The method according to claim 4, wherein analyzing the motion of the wall comprises find a location of scar tissue in the wall responsively to the motion.

7. The method according to claim 4, wherein analyzing the motion of the wall comprises comparing the motion of two or more chambers of the heart so as to detect improper synchronization of the motion of the chambers.

8. The method according to claim 1, wherein capturing the sequence of the two-dimensional ultrasound images comprises capturing the images from multiple different positions of an acoustic transducer, and wherein the method comprises reconstructing a sequence of three-dimensional images showing the motion of the organ based on the two-dimensional ultrasound images.

9. A method for diagnosis of a beating heart, comprising: providing a catheter having a position sensor configured to transmit signals used to determine location and orientation coordinates of a distal end of the catheter in a 3-D coordinate frame of reference and an ultrasonic imaging sensor configured to transmit and receive signals used to determine two-dimensional (2D) ultrasound images;

inserting the catheter into a chamber of the beating heart;

capturing on an image processor multiple sequences of ultrasound input images of the beating heart using the catheter in the chamber of the heart of a patient, each of the ultrasound input images being associated with a point in time relative to an annotation point in the heart cycle and a location and orientation coordinate of the distal end of the catheter at the point in time relative to the annotation point in time;

collecting data that are indicative of respective local values of a physiological parameter at locations on a surface of the beating heart;

creating an electroanatomical map of the chamber of the beating heart within the 3-D coordinate frame of reference using the data that are indicative of respective local values of the physiological parameter at locations on the surface of the beating heart;

displaying a video of the sequence of 2D images in succession to show motion of the beating heart;

freezing the video to display one of the 2D images of the sequence;

identifying at least one contour of the beating heart on the one frozen image;

finding the identified at least one contour in each of the other images in the sequence of 2D images;

analyzing changes in the identified at least one contour in the sequence of 2D images based on the motion of the beating heart by computing a displacement of the at least one contour over a period of cyclical movement of the beating heart;

generating an output in response to analyzing changes of the identified at least one contour;

displaying the output on the video of the sequence of 2D images; and superimposing an indication of changes in the local values on the surface in the three-dimensional images as the beating heart moves in the three-dimensional images in the sequence on the video by overlaying the electroanatomical map on the video of the motion of the beating heart using the location and orientation coordinates of the distal end of the catheter at each point in time relative to the annotation point in time.

10. The method according to claim 9, wherein the ultrasonic imaging sensor further comprises an acoustic transducer, and capturing the multiple ultrasound input images comprises capturing two-dimensional ultrasound images from multiple different positions of the acoustic transducer, and recording location and orientation coordinates of the acoustic transducer in the multiple different positions, and wherein generating the sequence comprises combining the two-dimensional ultrasound images using the location and orientation coordinates to reconstruct the three-dimensional images.

11. The method according to claim 10, wherein capturing the two-dimensional ultrasound images comprises recording respective times of capture of the two-dimensional ultrasound images relative to an annotation point in a cycle of motion of the beating heart, and wherein combining the two-dimensional ultrasound images comprises grouping the two-dimensional ultrasound images according to the respective times of capture in order to generate the three-dimensional images corresponding to the respective times in the cycle.

12. The method according to claim 11, wherein capturing the two-dimensional ultrasound images further comprises using the transducer while tracking location and orientation coordinates of the catheter using the position sensor.

13. The method according to claim 9, wherein generating the sequence comprises coloring the surface of the beating heart in the three-dimensional images responsively to the values of the physiological parameter.

14. The method according to claim 13, wherein collecting the data comprises collecting electrical data, and wherein coloring the surface comprises displaying variations in electrical activity of the heart over an area of a chamber of the heart in the course of one or more heart cycles.

15. Diagnostic apparatus, comprising:
a catheter having a position sensor configured to transmit signals used to determine location and orientation coordinates of a distal end of the catheter in a 3-D coordinate frame of reference and an acoustic transducer configured to transmit and receive signals used to determine two-dimensional (2D) ultrasound images, the acoustic transducer configured to capture a sequence of two-dimensional ultrasound images of a beating heart within a body of a patient in the 3-D coordinate frame of reference; and
an image processor, which is configured to associate each of the two-dimensional (2D) ultrasound images with a point in time relative to an annotation point in the heart cycle and a location and orientation coordinate of the distal end of the catheter at the point in time relative to the annotation point in time, and create an electroanatomical map of a chamber of the beating heart within the 3-D coordinate frame, wherein the image processor is also configured to: (i) display a video of the sequence of 2D images in succession to show motion of the organ and overlay the electroanatomical map on the video of the motion of the beating heart using the location and orientation coordinates of the distal end of the catheter at each point in time relative to the annotation point in time; (ii) freeze the video to display one of the 2D images of the sequence; (iii) identify at least one contour of the organ beating heart on the one frozen image; (iv) find the at least one contour in each of the other images in the sequence of 2D images; (v) analyze changes in the at least one contour in the sequence of 2D images based on the motion of the beating heart by computing a displacement of the at least one contour over a period of cyclical movement of the beating heart; (vi) generate an output in response to analyzed changes of the at least one contour; and (vii) display the output on the video of the sequence of 2D images.

16. The apparatus according to claim 15, wherein the image processor is configured to compute at least one parameter, selected from a group of parameters consisting of a displacement of the contour over a period of cyclical movement of the beating heart, a velocity vector of one or more segments of the contour, and a strain in the beating heart responsively to a change in length of the contour.

17. The apparatus according to claim 15, wherein the image processor is configured to analyze the motion of a wall of at least one chamber of the heart over one or more cycles of the heart.

18. The apparatus according to claim 17, wherein the catheter is configured to be inserted into the heart so as to capture the two-dimensional ultrasound images using the acoustic transducer while tracking location and orientation coordinates of the catheter using the position sensor.

19. The apparatus according to claim 17, wherein the image processor is configured to indicate a location of scar tissue in the wall responsively to the motion.

20. The apparatus according to claim 17, wherein the image processor is configured to display the motion of two or more chambers of the heart so as to provide an indication of improper synchronization of the motion of the chambers.

21. The apparatus according to claim 15, wherein the acoustic transducer is operable to capture the images from multiple different positions of an acoustic transducer, and wherein the image processor is configured to reconstruct a sequence of three-dimensional images showing the motion of the organ based on the two-dimensional ultrasound images.

22. Diagnostic apparatus, comprising:
an invasive probe comprising a position sensor configured to transmit signals used to determine location and orientation coordinates of a distal end of the probe in a 3-D coordinate frame of reference and an acoustic transducer configured to transmit and receive signals used to determine two-dimensional (2D) ultrasound images, the acoustic transducer also configured to capture multiple ultrasound input images of a beating heart within a body of a patient, the invasive probe, also configured to collect data that are indicative of respective local values of a physiological parameter at locations on a surface of the beating heart; and
an image processor which is configured to associate each of the two-dimensional (2D) ultrasound images with a point in time relative to an annotation point in a heart cycle of the beating heart and a location and orientation coordinate of the distal end of the catheter at the point in time relative to the annotation point in time, and create an electroanatomical map of a chamber of the beating heart within the 3-D coordinate frame, wherein the image processor is also configured to (i) display a video of the sequence of 2D images in succession to show motion of the beating heart and overlay the electroanatomical map on the video of the motion of the beating heart using the location and orientation coordinates of the distal end of the catheter at each point in time relative to the annotation point in time; (ii) freeze the video to display one of the 2D images of the sequence; (iii) identify at least one contour of the beating heart on the one frozen image; (iv) find the at least one contour in each of the other images in the sequence of 2D images; (v)_analyze changes in the at least one contour in the sequence of 2D images based on the motion of the beating heart by computing a displacement of the at least one contour over a period of cyclical movement of the beating heart; (vi) generate an output in response to analyzing changes of the at least one contour; (vii) display the output on the video of the sequence of 2D images; and (viii) superimpose an indication of changes in the local values on the surface in the three-dimensional images as the beating heart moves in the three-dimensional images in the sequence on the video.

23. The apparatus according to claim 22, wherein the ultrasound input images comprise two-dimensional ultrasound images, which are captured from multiple different positions of the acoustic transducer, and wherein the image processor is coupled to receive location and orientation coordinates of the acoustic transducer in the multiple different positions, and to combine the two-dimensional ultrasound images using the location and orientation coordinates in order to reconstruct the three-dimensional images.

24. The apparatus according to claim 23, wherein the image processor is configured to record respective times of capture of the two-dimensional ultrasound images relative to an annotation point in a cycle of motion of the beating heart, and to group the two-dimensional ultrasound images according to the respective times of capture in order to generate the three-dimensional images corresponding to the respective times in the cycle.

25. The apparatus according to claim 24, wherein the apparatus comprises a catheter, which comprises the acoustic transducer and a position sensor and is configured to be inserted into the heart so as to capture the two-dimensional ultrasound images using the transducer while tracking coordinates of the catheter using the position sensor.

26. The apparatus according to claim 25, wherein the catheter is the invasive probe and is configured to collect the data from an inner surface of the heart.

27. The apparatus according to claim 22, wherein the image processor is configured to color the surface of the moving organ in the three-dimensional images responsively to the values of physiological parameter.

28. The apparatus according to claim 27, wherein the data comprises electrical data, and wherein the image processor is configured to color the surface so as to display variations in electrical activity of the heart over an area of a chamber of the heart in the course of one or more heart cycles.

* * * * *